United States Patent
Encaoua et al.

(10) Patent No.: US 9,726,911 B2
(45) Date of Patent: Aug. 8, 2017

(54) METHOD FOR ESTIMATING A REFERENCE POSTURE

(75) Inventors: David Encaoua, Carrières sur Seine (FR); Pascal Thomet, Paris (FR)

(73) Assignee: INTERACTIF VISUEL SYSTEME (I V S), Clichy (FR)

( * ) Notice: Subject to any disclaimer, the term of this patent is extended or adjusted under 35 U.S.C. 154(b) by 1244 days.

(21) Appl. No.: 13/806,126

(22) PCT Filed: Jun. 21, 2011

(86) PCT No.: PCT/EP2011/060304
§ 371 (c)(1),
(2), (4) Date: May 24, 2013

(87) PCT Pub. No.: WO2011/161087
PCT Pub. Date: Dec. 29, 2011

(65) Prior Publication Data
US 2014/0148707 A1   May 29, 2014

(30) Foreign Application Priority Data

Jun. 21, 2010 (FR) ...................................... 10 02603
Aug. 30, 2010 (FR) ...................................... 10 56873

(51) Int. Cl.
| | | |
|---|---|---|
| A61B 3/00 | (2006.01) | |
| A61B 3/10 | (2006.01) | |
| G02C 13/00 | (2006.01) | |
| A61B 5/11 | (2006.01) | |
| A61B 5/00 | (2006.01) | |

(52) U.S. Cl.
CPC .......... *G02C 13/003* (2013.01); *A61B 5/0077* (2013.01); *A61B 5/1116* (2013.01); *A61B 5/1128* (2013.01); *A61B 5/6803* (2013.01); *A61B 5/6814* (2013.01); *A61B 5/742* (2013.01)

(58) Field of Classification Search
CPC ....................................................... G02C 7/027
USPC ................ 351/200, 205, 209–211, 221, 222, 351/243–246
See application file for complete search history.

(56) References Cited

U.S. PATENT DOCUMENTS

| | | | | |
|---|---|---|---|---|
| 6,257,721 B1 * | 7/2001 | Hayashi | ................. | A61B 3/112 351/204 |
| 9,195,078 B2 * | 11/2015 | Haddadi | .................. | A61B 3/11 |
| 2004/0061831 A1 * | 4/2004 | Aughey | ................. | A61B 3/113 351/209 |

(Continued)

FOREIGN PATENT DOCUMENTS

| | | |
|---|---|---|
| EP | 1747750 | 5/2005 |
| EP | 1591064 | 11/2005 |
| FR | 2892529 | 4/2007 |

*Primary Examiner* — Brandi Thomas
(74) *Attorney, Agent, or Firm* — Blakely Sokoloff Taylor & Zafman LLP

(57) ABSTRACT

The invention relates to a method for estimating a reference posture of a subject with a view to taking measurements in order to determine the parameters for manufacturing a vision correction device, including, for a plurality of instances in which the head reaches a target reference posture from at least one deviated posture, the steps of: measuring the actual reference posture to thus obtain a plurality of sets of actual reference posture data, and storing said sets of data in a memory; and processing said sets of actual reference posture data using a digital processing unit in order to obtain an optimal reference posture.

18 Claims, 3 Drawing Sheets

(56) References Cited

U.S. PATENT DOCUMENTS

2009/0262302 A1* 10/2009 Chauveau ............ G02C 13/005
  351/204
2010/0114502 A1* 5/2010 Badami .................. F03D 17/00
  702/35

* cited by examiner

METHOD FOR ESTIMATING A REFERENCE POSTURE

This is a non-provisional application claiming the benefit of International Application Number PCT/EP2011/060304 filed Jun. 21, 2011.

The invention relates to analysis of the visual behaviour of a subject, for the purposes of personalisation and optimisation of the optical characteristics of corrective lenses or ophthalmic lenses which the subject must wear, as well as their mounting on the frame.

More precisely, the invention relates to the analysis of the general posture of the head of the subject and the taking of measurements performed by an optician who proceeds with acquisition of data necessary for determining the general implantation configuration of the corrective lenses with respect to the eyes of the subject.

Numerous systems aiming to optimise the position of lenses in a frame relative to the relative position of the pupils of the eyes of the subject and of the frame are known already. For this purpose, fixed or animated images of the face wearing the frame are taken by a camera, and detection of the position of the eyes is carried out, as is detection of the placement of the frame.

In particular, document FR-2860887A in the name of the applicant discloses a system in which, from a series of animated images of the face of the subject during movement in front of a fixed camera, a reference image is determined in which the face is best focussed on the camera so as to have the best definition of the relative position of the eyes and of the frame.

At the same time, manufacturers of ophthalmic lenses these days endeavour to optimise the design of these lenses, especially in so-called progressive lens technology, by examining the behaviour of the subject when his look shifts. For example, document FR-2892529A in the name of the applicant divulges a system comprising:
  a camera,
  a screen for displaying the images taken by the camera,
  an accessory 20 capable of being worn fixed to the head of the subject and bearing a plurality of visual markers 21,
  means forming visual target(s) likely to cover at least two determined positions relative to the camera, and
  image analysis means capable of analysing the position of the visual markers in the images taken by the camera. The image analysis means deduce the position and the orientation in space of the accessory 20, and therefore of the head of the subject, when he observes different regions of means forming visual target(s), to deduce therefrom especially information on the relative importance of the movement of the head during displacement of the vision from one target to the other, as well as the relative importance of the movement of the eyes.

Figure 1:
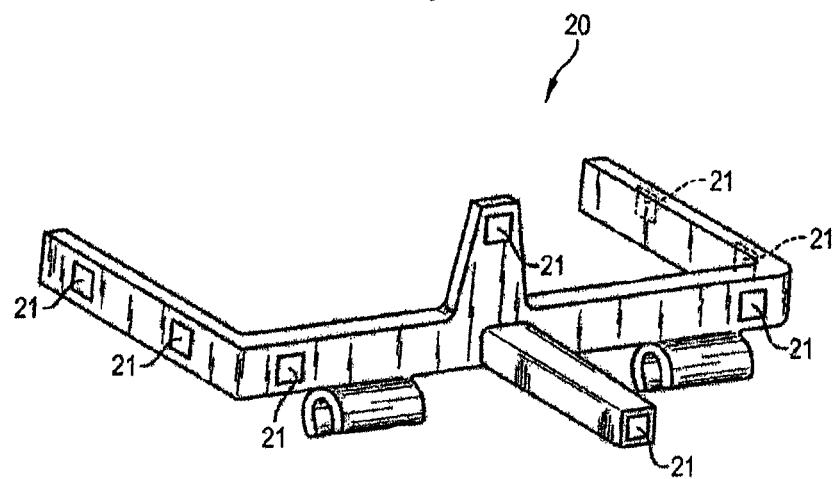

Typically, the accessory 20 can conform to the accessory illustrated in FIG. 1 and comprise means forming geometric indicators 21 selected specifically to enhance the orientation of the frame. It can comprise a longilinear support bearing a series of visual markers 21, placed along the branches of the frames and/or on the upper front upright of the frame.

For measurements to be precise, it is necessary for the head of the subject to be in a reference posture, and looking in a defined position, adapted to taking measurements.

The reference posture can especially be the distant vision posture in which the wearer is in a natural position and fixes a point in infinity right in front of him in a horizontal plane. By way of variant, the reference posture can correspond to a near-vision posture, such as the reading position, that is, the position in which the subject fixes a point at around forty centimeters from his eyes and lowers his look by 30° relative to the horizontal plane.

Throughout this description, the reference posture will correspond to the distant vision posture. This is however not limiting and is given only by way of example. When the optician measures the relative position of the pupils relative to the frame, it is indispensable that he ensures the wearer is in a posture near this reference posture.

Currently known systems do not precisely and automatically determine if the posture of the subject is near the reference posture. This is therefore generally done manually by the optician himself from simple observation of the posture of the subject at the moment when measurements are taken. For this, the optician can especially be aided by the systems described previously, giving a value of the inclination of the accessory fixed on the frame.

The posture of the subject can for example be described (non-limiting) by means of two angles for a direction of the known look. The first angle corresponds to the cap of the head, that is, an oriented angle which reflects the fact that the subject tends to have his head more or less turned to left or right when he is looking at an object placed right in front of him.

The second angle corresponds to the inclination of the head, that is, an oriented angle which reflects the fact that the subject tends to have his head more or less lifted or lowered when looking at an object placed right in front of him. For a given frame, this second angle can be measuring the pantoscopic angle, that is, measuring the inclination of the middle plane of the corrective lens relative to the vertical.

To determine the distance between the pupils of the subject (one of the parameters for producing correction devices), the optician generally uses a pupillometer. In this case, the cap is arbitrarily supposed to be zero since the pupillometer is supported against the front of the subject. However, this device do not take into account the pantoscopic angle which must be measured separately, or, if required, of the fact that the subject can carry his head to the side (tendency of the subject to look rather to the right or left in his reference position).

However, this approach does not guarantee that the position assumed by the subject corresponds to his natural reference position and is not influenced by the presence of the optician especially, a particular object in the room or the immediate psychological state of the subject (shop effect which can intimidate the subject, stress associated with demands by the optician, etc.). For example, if the wearer lowers his head too much during taking of measurements, excessive height measurement values will result. In the case of progressive lenses (for which the corrective power varies from high to low), he could have his eyes closely opposite the correction zone, whereas the object he is looking at is far away.

The natural reference posture is however of major importance since it determines the manner in which the wearer will project his look onto the lenses of glasses in his position of maximum comfort. Poor posture therefore leads to poor centring measurements of the lenses. It is therefore paramount to select a correct image posture for calculation of the projection of the look onto the glasses lenses and therefore evaluate the quality of the posture of the wearer during measurement.

By way of digital illustration, the consequence of an error of one degree on the orientation of the head is a centring error of around 0.4 millimeters, while the preferred precision must be less than half a millimeter.

An approximation of the inclination in the reference posture in distant vision can also be realised by reference to the Frankfurt plane which can be defined by the tragions and the bottom of the ocular orbits. A first approach for measuring the Frankfurt plane is to use the two rotation centres of the eye to determine a first axis which will be by definition parallel to the Frankfurt plane and to a known distance, of around 22 millimeters from the Frankfurt plane. Next, the position of at least one tragion is placed manually, automatically or semi-assisted on at least two images of the face of the subject wearing an accessory 20 such as that defined earlier. Since the points of the tragion are (visible) reference points and the tragion is immobile in the marker of the accessory 20, it can be positioned in three dimensions as being the intersection of the two observation lines passing through the tragions and the optical centre of the camera. The Frankfurt plane can easily be calculated as being the plane containing the tragion and tangential to the cylinder.

This plane is deemed horizontal when the subject is in a distant vision position. This measurement is morphological and independent of the posture of the subject during measuring. However, this approach does not guarantee that the natural position in distant vision coincides perfectly with a horizontal Frankfurt plane.

The invention therefore aims to propose a process for precisely determining a natural reference position of the subject, fully or partly automatically.

For this, the invention proposes a process for estimation of a reference posture of a subject in light of taking measurements for determining parameters for manufacturing a vision correction device, comprising the steps, for a plurality of arrivals of the head at a target reference posture from at least one deviated posture consisting of:
  measuring the real reference posture during each arrival at the target reference posture to obtain several sets of data of real reference posture, and store said sets of data,
  processing said sets of data of real reference posture by means of a digital processing unit to produce an optimal reference posture.

The chaining of these steps produces an optimal reference posture, and this despite the fact that each deviation increases dispersions and therefore the variability of the way the head is carried. Using repeated deviations was therefore something the expert would have wanted to avoid.

Some preferred, though non-limiting, aspects of the process according to the invention are the following:
  the real reference posture is measured during arrival of the head at the target reference posture;
  at least two real reference postures are measured corresponding to two opposite deviated postures, and the optimal reference posture is obtained by taking an average of the reference postures measured during these two opposite deviated postures;
  the process also comprises obtaining a confidence interval on said optimal reference posture;
  the target reference posture corresponds to a posture in which the subject is naturally looking at a determined target;
  the reference posture corresponds to the distant vision or near vision posture of the subject;
  the posture data comprise a pantoscopic angle and cap value of the head of the subject;
  the pantoscopic angle and cap values are determined by means of conditional probabilities depending on the previous sets of data of real reference posture and/or of the type of previous deviated posture;
  the process also comprises the application of weight to the data as a function of their respective pertinence for evaluation of the optimal reference posture and of the confidence interval;
  the process also comprises a step for determining the Frankfurt plane of the subject;
  data of the Frankfurt plane are also integrated into the data taken into account for determination of the optimal reference posture and he confidence interval;
  the process also comprises extrapolation of supplementary data relative to reference postures which have not been taken by the subject from recorded data;
  measuring the real reference posture comprises the location of singular points on at least one image of the subject;
  the singular points are supported by an accessory fixed on a glasses frame worn by the subject;
  the process also comprises editing of posture data used for calculating the production parameters of the correction device, from:
  the confidence interval and the optimal reference posture of a set of data of a real reference posture or extrapolated from the sets of real data,
  presentation of an image of the subject in this posture and/or of the impact of the choice of this posture on the production parameters of the correction device.

According to a second aspect, the invention proposes a system for estimating a reference posture of a subject adapted to be implemented in a process according to the invention, comprising:
  means for measuring, during each arrival at the target reference posture, the real reference posture, to obtain several sets of data of real reference posture,
  means for storing said sets of data,
  a digital processing unit adapted to process said sets of data of real reference posture to produce an optimal reference posture.

Some preferred, though non-limiting, aspects of the system are the following:
  the digital processing unit also obtains a confidence interval on said optimal reference posture;
  the system also comprises a portable display device adapted to be worn by the subject, and in that the measuring means comprise an image-capture device, fixed relative to the portable display device; and
  the display device also comprises visual targets. According to a final aspect, the invention proposes a computer program product comprising program code instructions for execution of the steps of the process described hereinabove, when said program is executed by a computer.

Figure 2:
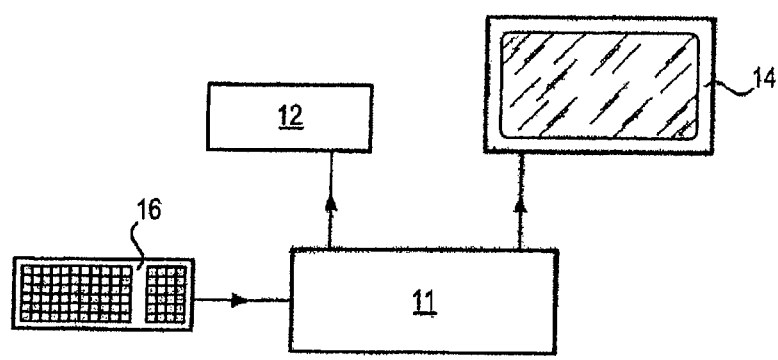
Figure 3:
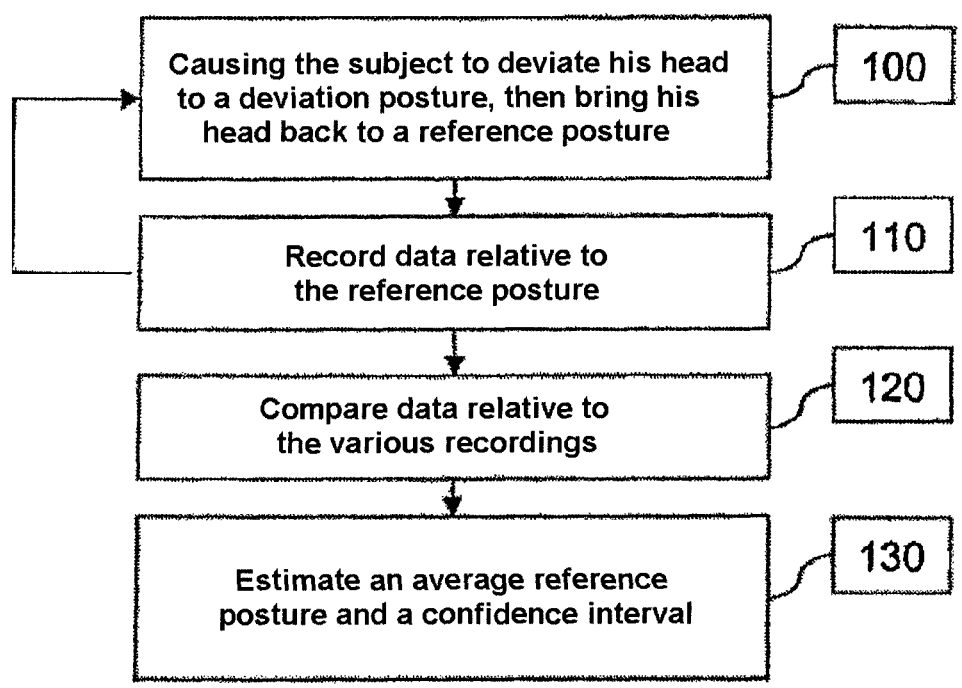
Figure 4:
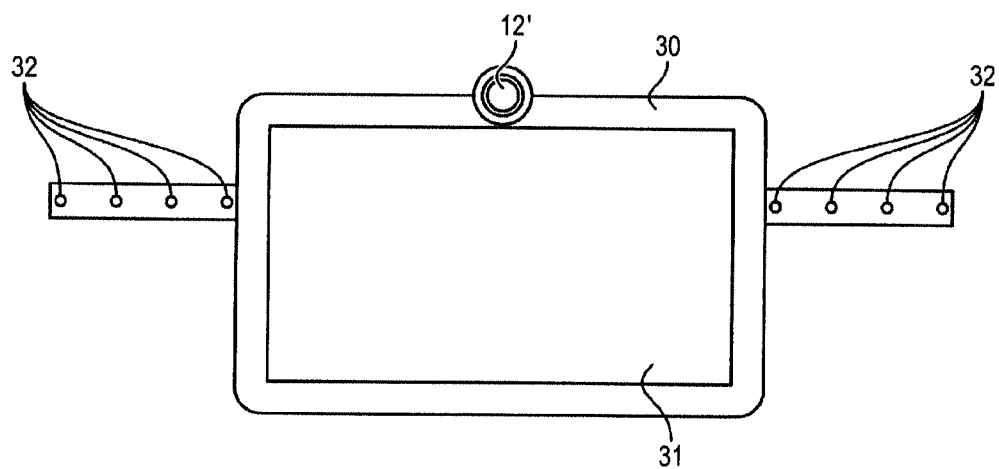

Other characteristics, aims and advantages of the present invention will emerge more clearly from the following detailed description and with respect to the attached diagrams given by way of illustrative examples and in which:

FIG. 1 illustrates a perspective view of an example of accessory which can be used in executing the system and the process according to the invention, FIG. 2 illustrates a block diagram of different components of the system of the invention, and FIG. 3 is a graphic representation of the different steps according to an embodiment of the invention, and FIG. 4 is a frontal view of an example of a portable system which can be used in executing the system and the process according to the invention.

As illustrated in FIG. 2, a system according to the invention comprises for example a frame in the upper region of which are housed an image-capture device 12 such as a camera, placed near a device for obtaining a target which the subject will fix in the reference posture, such as a two-way mirror placed in front of the camera. The camera 12 is attached to a central unit 11 for acquisition of video images. A keyboard 16, as well as any other input and output device such as a mouse, a screen 14, etc. controls the system.

For example, it is possible to integrate the invention in the device marketed under the name Activisu Expert 3 by the applicant. Such a device comprises a two-way mirror positioned vertically. The camera is placed behind the mirror such that the position of its principal optical axis relative to the mirror is known. Typically, the camera is arranged such that its principal optical axis extends substantially perpendicularly to the mirror.

Also, the accessory 20 has the form of a clip and is placed on the frame.

For more details on the system, reference could be made for example to the previously cited applications FR-2860887A or FR-2892529A.

By way of variant, it is not necessary to start out from an image (or any other information useful for centring measurements) for each posture measurement. It is possible for example to employ a system for tracking the position of the head in real time (or delayed calculation) linked to photo apparatus. The posture will then be studied with a large number of measurements of the posture while only one (or some) photo(s) will be taken for centring.

Examples of systems for tracking the position of the head can be the following, in a non-limiting manner:

An accelerometer placed fixed relative to the head. After appropriate calibration continuous acquisition of the acceleration produces tracking of the position of the head.

An ultrasound system such as the Vision Print System marketed by the company Essilor, for measuring the eye-head coefficient for the personalisation of the Ipseo lens.

Infrared transmitters placed on the head of the subject, for example on an accessory 20 of the type described previously or on any object fixed relative to the head which is equivalent, linked to an infrared camera. The system is similar to the Activisu Expert 3 system, but uses an infrared camera instead of a camera sensitive only to the visible spectrum, and by using markers transmitting in the infrared spectrum in place of using visual markers of a determined colour (green on the Activisu Expert 3 system).

Any system of three-dimensional reconstruction of the face for obtaining a posture parameter sufficiently precise for study, this parameter able to be rotation of the head about the vertical axis (the cap) or about the horizontal axis oriented right/left (linked to the pantoscopic angle). This can be three-dimensional reconstruction of salient points of the face by stereoscopy (or photogrammetry) by means of two cameras (or reconstruction with a single camera linked to scaling means sufficiently precise for study (the scaling means can be for example a known distance between two of the salient points identified on an image).

During measuring by one of these devices for tracking posture, a link is also made between these measurements and an image of the subject to calculate the optimal posture.

To determine the natural posture of the subject, the process according to the invention comprises especially the iteration of steps taken by means of pictures (or an equivalent device for tracking position) and calculation of optimal posture from these pictures.

According to an embodiment, the process comprises the steps consisting of initially recording 110 a plurality of postures of the subject by the camera 12, and at each recording step having the wearer perform at least one determined movement before returning to a given reference posture 110.

For example, the postures recorded can correspond to the posture at a given instant of the subject when he looks at himself in the mirror. Then, by means causing a spontaneous shift such as verbal instructions, messages displayed on a screen, switching on a light at a given location in the room to attract the look of the subject, or more generally any means causing the patient to modify his posture, displacement of the subject or at least rotation of his head is caused 110 before returning it to the initial reference position in which he looks at himself in the mirror.

Typically, it is possible to ask the subject to turn his head to right or left, to look at the floor or the ceiling, to read a document, to close his eyes, the basic idea being to distract him temporarily to "reinitialise" his posture and come back to his natural posture, despite the environment and his psychological state. In this way the subject is encouraged to direct his look right in front of him generally more naturally at each iteration. Improvement is not however guaranteed at each iteration, to the extent where the subject can for example show fatigue which will cause him to modify his reference position.

This is why the use of statistical estimation implemented on the basis of the different postures is preferred over selection of the last posture measured.

In the case where the reference posture corresponds to near vision in the reading position, the subject fixes a target and measurements are taken to evaluate the distance between the target and the frame worn by the subject, the cap, and the angle formed by the inclination of the central plane of the corrective lenses relative to the vertical plane containing the direction of the look of the subject when he fixes the target (the pantoscopic angle being particular to distant vision).

For this, the target can be on a tablet 30, and the position of the frame is determined by means of the accessory 20 fixed on the latter.

Here, the tablet 30 is a portable system fitted with a display device 31 such as a liquid crystal screen, and on which is mounted a device for taking an image 12', such as a camera.

The screen can for example measure around 40 cm wide by 25 cm high.

Advantageously, this tablet 30 positions the subject by the latter. The person can therefore be positioned facing the tablet 30, and therefore facing the camera 12', the tablet 30 advantageously replacing a mirror or any other device aiding positioning.

The subject can grip the tablet 30 in his hands, such as he would a book or a newspaper, such that he can comfortably fix on the elements displayed by the screen 31.

It is possible for example to display one or more texts, images, ads, fixed or mobile on the screen.

Typically, the screen 31 can display information on lenses and existing lenses. It can also send the subject the image taken by the camera to improve its centring, for example.

The operator can take his measurements by asking the subject to view the elements displayed on the screen 31, then a location of his choice in the room, etc. so as to determine by means of the camera 12' mounted on the screen 31 and/or the camera 12 the reference posture in the reading position of the subject.

According to another embodiment, the tablet 30 itself comprises means for distracting the subject to bring him back to his natural reference posture.

Typically, the tablet 30 can display text stretching right across width of the screen 31. In this way, when the subject reads the text displayed, his look travels across the screen and his head makes a left/right and up/down rotation movement. It is then possible to determine the reference posture of the subject, to the extent where the movement of the head caused by reading the text constitutes sufficient distraction to reinitialise the posture of the subject in the reading position: in fact, when the latter then fixes a target element on the tablet 30, such as a centred image or a light-emitting diode fixed relative to the screen 31, his position is more natural than prior to reading.

The reference posture in the reading position can be determined approximately as being the average between the extreme reading postures of the text on the screen 31. Because of the display of the text by the screen 31, it is also possible to measure an eye-head coefficient (that is, an average ratio between the angle of rotation of the eye and the rotation of the head of the subject), by determining, with the camera, the angular interval of the head of the subject: because the distance between the head of the subject and the width of the screen is known, the angular interval travelled by the eyes of the subject is deduced therefrom during reading, as well as the eye-head coefficient.

By way of variant, text is displayed at different points of the screen and/or in different sizes to cause the subject to look at different points on the screen before returning to the target element. In-depth behavioural study is also possible if the target remains substantially accurate (for example very brief text) and moves into varied reading positions (up, down, right or left), the screen 31 being controlled by the processing unit 11; it is possible to know at any moment how the way the head is carried evolves as a function of shifts by the target.

According to yet another variant, apart from the visual targets displayed by the screen 31 the tablet 30 can comprise visual targets 32 such as light-emitting diodes (LED) fixed relative to the screen. An audio signal can accompany the on/off switching of targets.

For example, two sets of LEDs can be fixed to arms which extend radially from the lateral sides of the tablet 30, so as to create three sets of visual targets 32 for the subject.

In this case, each arm comprises four LEDs, separated from each other by a distance of between approximately 0.5 cm and 5 cm, preferably around 2 cm. Advantageously, using a plurality of adjacent LEDs on each arm adapts the angular spread between the accessory (and therefore the head of the subject) and the visual lateral target (i.e. here the LED lit during measuring) as a function of the distance between the tablet 30 and the accessory 20.

By way of variant (non illustrated in the figures), the tablet 30 has no screen, comprising three sets of LEDs, a central and two lateral.

So that measurements of the eye-head coefficient and the cap can be taken and the natural posture of the subject can be determined, the visual targets 32 merely have to be lit successively, preferably randomly.

During these steps, acquisition and automatic analysis of recorded data is carried out and it is no longer necessary to refer to the sole expertise of the optician.

Calculation of the "optimal" reference position 130 is performed from observations and recordings, where a position can be different to the positions observed and correspond to an intermediate or extrapolated position.

This process is based on the use of a model of human behaviour viewed by the device for interpreting measurements of postures.

It can especially take the form of conditional probabilities, for example the probability of having an optimal reference posture p, knowing that there is a sequence of postures pi measured after i iterations, and knowing the types of deviation used (looking up, left, reading a document, etc.) prior to each posture pi. For example, studies have shown that the probability that the cap of the head is good is stronger once the head has been turned right then left than prior to these movements. The measurements of the cap obtained after these movements will therefore have a higher weight in calculations of this value. Similar considerations can be made advantageously for the pantoscopic angle after the ceiling has been looked at.

The model of human behaviour viewed by the device could especially use the range of mathematical tools of statistics of the prior art and especially:

conditional probabilities, for example the probability of having a posture p knowing that there is a sequence of postures pi, and depending on the types of deviation used (looking up, left, reading a document, etc.) prior to each posture pi: these conditional properties could be organised in a Markov chain.

advanced analyses for detecting whether a value is "coherent" or "aberrant" and accordingly censuring aberrant values Bayesian networks could be used for example to determine the instruction sequence of deviations to be given as a function of postures previously observed and previously given deviation instructions.

Bayesian probabilities (or any other adapted statistical tool) could model for example the correlation between a posture or an external posture parameter and the parameters of reference postures. This external posture or this external posture parameter could for example be: reading vision posture during an attempt to measure distant vision posture. The eye-head coefficient—measured by a system such as Activisu Expert 3 developed by the applicant, or the Vision Print System developed by Essilor—specifically the percentage of rotation of the head relative to the rotation of the eye when an object placed at 40° on the side of the head is looked at.

The result obtained is in the form of an "optimal" value and an interval of possible values.

Posture value means here especially the value of the pantoscopic angle and of the cap for a given posture.

The model of human behaviour viewed by device can also be completed by an "a priori" model, in particular for measuring the cap, to reduce the number of samples necessary for determination of the natural reference posture of the subject. Such an "a priori" model can for example be used to improve calculation of the maximum likelihood by Bayesian inferences, especially counting on a reference posture rather than another, in particular when the postures taken by the subject are highly unstable, drawing on statistical analyses.

For example, it is known that the cap of a person is generally closer to 0° than 3°. As a consequence, using the a priori model involves selecting a reference posture close to 0° rather than 3° in case of instability of measurements.

According to an embodiment, use of such an a priori model is progressive. In this way, the stabler the measurements taken on the subject, the less used the a priori model is. And on the contrary, the unstabler the measurements taken, the more preferred the a priori model, the average of measurements not being sufficiently pertinent due to their dispersion.

Determining the natural "optimal" reference posture is more reliable.

Using the a priori model can also be adapted to measuring the pantoscopic angle. It is however more difficult than in the case of measuring the cap, given that the pantoscopic angle can vary between 2 and 18°, instead of 0-3° for the cap, and that it depends inter alia on the frame and the way the head of the subject is carried. Typically, when measurements are taken for progressive lenses, an a priori model can prefer high values for the pantoscopic angle to release distant vision of the subject, taking into account the posture after the head is raised (when shifting from the reading position to the distant position).

The optician can use his expertise or select the best posture from the possible values proposed, and the system can display in real time the impact of a choice of posture value on the results of measurements to aid the optician in his decision.

By way of variant, the display is delayed, for example on completion of the recording of the series of postures pi.

It is also possible to display an image representing the posture of the wearer corresponding to a possible posture value selected by the optician to help verify that this value corresponds to the posture which he observes on the wearer or which he wants to use for the centring.

This image can be the most representative image among those recorded during measuring (measuring of the posture and centring measuring). By way of variant, the image displayed can result from production of a synthesis image of the posture, in creating a three-dimensional reconstruction from real images and interpolating the images recorded during iteration.

For example, it is possible to take the average (which could be weighted by conditional probability criteria obtained using statistical tools) as "optimal" value and using the type of spread to calculate a confidence interval as an interval of possible values.

By way of option, if the dispersion of the pantoscopic angle (high/low inclination) is excessive, it can be proposed to the user to measure the Frankfurt plane, for example by determining the position of the eye and of the tragion, and to use them to improve the possible values and the optimal value.

By way of default, the value of the Frankfurt plane can be taken for example as an optimal value, or it can be used to detect values of aberrant measurements to censure and reduce dispersion. The precision of the Frankfurt plane can also be estimated and optionally considered in statistical calculations, especially with a weight greater than the values considered as less pertinent.

For example, in terms of measuring the natural posture in distant vision, the invention can comprise the following steps.

The optician places the subject in front of the mirror.

The subject preferably wears the accessory 20 formed by means forming geometric indicators 21.

Indications of "deviation" are given to the subject (step 100): they are for example displayed on the screen and repeated by the optician, or announced by loudspeaker, and the optician ensures that they are executed. The instructions will consist for example of asking to look at the bridge of the frame in the mirror (or any other target for distant vision) to determine a first reference posture, then asking to follow indications of deviation to bring the subject to a deviated posture (freely turning the head to right or left, freely lifting or lowering the head, turning towards the optician (who can be standing behind the subject), closing the eyes, moving and heading towards another place before facing the mirror again, etc.).

The subject is then asked to resume his reference posture, for example by again fixing on the bridge of the frame in the mirror, and the new reference posture is recorded (step 110).

This operation (deviation then return to the reference posture and recording of this last reference posture) is repeated at least once, preferably several times.

By way of variant, the recorded reference posture corresponds to a deviated posture of the subject, that is, a posture in which the latter fixes on a given target (for example right or up). The operator then asks the subject to fix on a second target, in the opposite direction (for example left or down, respectively). The reference posture of the subject (taken into account for determination of the "optimal" natural posture) corresponds to an average (which can be weighted) of these two deviation postures.

Of course, postures can be recorded continuously, without the deviated posture for which measuring is performed necessarily corresponding to the extreme position of deviation, due to the continuous taking of images done by the camera. So, for example it is possible to ask the subject to make a continuous right/left rotation movement of the head and record two deviation postures, one right and the other left, which do not correspond to the extreme postures of the rotation movement. In this way, postures corresponding to the fixation of targets slightly offset to right and left (+/-6° for example relative to the posture at 0°) can be selected for example and the average can be taken to obtain the reference posture pi to be taken into account for calculations of the "optimal" value of the natural reference posture. To improve measurements, it is even possible to take several measurements between the two extreme points of the right and left deviation postures, then calculate an integrated average of these measurements to determine the reference posture pi.

This variant embodiment has the advantage of being less sudden for the subject and more reliable, since the subject no longer needs to reposition his head at the centre after each deviation. Also, deviation postures having low amplitude are preferred to remain within the comfort interval of the subject.

Advantageously, deviation operations differ from one iteration to the other. For example, it is possible to successively ask the subject to turn his head freely right, then left, then to look at the ceiling, the floor, read a document, the aim here being to reinitialise the reference posture (here, the posture corresponding to distant vision) to determine the natural posture of the subject.

Also, the choice of deviations as well as the adjustment of calculations can depend on the type of lens to be made for the frame of the subject and on the stability of his postures. For example, measurements taken for determining the pantoscopic angle can be preferred over measurements taken for the cap in the case of a progressive lens. In fact, values are generally more centred for the cap than for the pantoscopic angle, such that their dispersion is less.

This choice can be made in advance, at the beginning of measuring, or during the measuring process, as a function of the recorded postures. So, if it is noted that the posture is unstable when the subject raises or lowers his head, an extra up/down deviation is preferred to confirm the measurements of the pantoscopic angle, to the detriment of the others.

Acquisition in real time is carried out by recording the posture values pi after each deviation i, and by selecting the deviation indications as a function of the ways in which the head is carried, already observed. For example it is an advantage to ask the subject to turn his head several times to the right then left if his pantoscopic angle is highly unstable. By way of variant, it is also possible to ask the subject to raise and lower his head if the measurement of his cap shows that he is unstable; the inventors have in fact noted that for measuring the cap the subject tended best to replace his head after having made an up/down or down/up movement of the head than after several right/left movements. In fact, during right/left rotation movements of the head, the subject may tend to resist or on the contrary amplify the movement and stop beyond the natural posture when he returns to the reference position, effectively falsifying the results, whereas when the right/left rotation movement is followed by an up/down movement (or down/up), the cap corresponds substantially to that of the natural position.

The inventors have also noted that right/left deviations give an indication of the stability and the amplitude of the comfort zone of the cap, whereas up/down deviations give an indication on the stability and the amplitude of the comfort zone of the pantoscopic angle, and an up/down deviation tends to recenter the cap of the subject whereas a right/left deviation tends to recenter his pantoscopic angle.

Once the stability of the cap and of the pantoscopic angle of the subject are known, it is then possible to adapt the number of deviations and the type of deviations asked on the latter to best determine his reference posture. The optimal value of the natural posture is then calculated on the basis of the different recorded postures pi and the possible values (steps 120 and 130), for example the values contained in a confidence interval.

During the measuring process, the system could automatically detect the instants where the wearer approaches the reference posture (as opposed to moments where he has moved away because he is busy responding to a "deviation" instruction). This detection could be based especially on two indices:

a. The posture is sufficiently near the reference posture (limited to the cap angle and pantoscopic angle, position in delimited space: distance from the mirror, position up down right and left)

b. The position is stabilised: weak movements during a determined time lapse.

This detection will automatically aggregate the values of postures to be taken into account in the calculations of statistics and will allow an automated process.

For each posture it is possible to take the average and the type of spread on the video images, to extract a tendency of evolution on the average mobile, etc.

Results of centring and personalisation measurements (measuring the distance between the two pupils, the lens-to-eye distance, etc.) are determined from the optimal value of the natural posture.

According to an embodiment, the system edits the posture value among the possible values.

During this editing, the optician can interactively see the new values of the centring measurements, the quality of the selected parameters (cap and pantoscopic angle), and if required an image representing the posture of the wearer to verify that the parameters correspond to the posture which he observes on the wearer or which he wants to use for centring. For each posture it is possible to take the average and the type of spread on the video images, extract a tendency of evolution on the average mobile etc.

A weight is then applied to the values as a function of a given behavioural model. For example, a cap near zero will be more pertinent than a high value, and a cap recorded after a left/right rotation movement of the face followed by an up/down movement will be more pertinent than that measured directly following a left/right rotation movement, the up/down deviation tending to recenter the cap of the subject.

In the same way, the pantoscopic angle will be more natural after the wearer has turned his head freely up or down, more still after he has made these two movements, etc. Also, it is also possible to apply a weight to each value as a function of the type of deviation made and of the behaviour (stability). So, for evaluation of the cap, measurements taken after up/down deviations can have greater weight than measurements taken directly after a right/left deviation, since it is evident that these first measurements give results closer to the natural cap.

The results obtained are displayed, for example on the system screen.

Also, it can prove advantageous to offer the optician the possibility of editing the reference way the head is carried from a set of acceptable values and appreciate its impact on centring measurements. To qualitatively evaluate the pertinence of the selected way the head is carried, the system displays an image representative of the reference way the head is carried among the images recorded during the analysis phase, readjusted to the position of the eyes (so that moving from one image to the other is continuous) and interpolated to simulate a position between two (or more) recorded photos. Techniques such as optical flow or disparity map associated with warping or triangularisation and texture mapping can be used.

The images of postures can be extrapolated to simulate a position which was unable to be recorded (subject having a way the head is carried which is not at all natural in front of the mirror).

This extrapolation can especially be realised from the a priori model. It can also be displayed in three-dimensional stereoscopy for better viewing.

The invention claimed is:

1. A process for estimation of a reference posture of a subject for the purposes of taking measurements for determination of parameters for the manufacture of a vision correction device, comprising the steps, for a plurality of arrivals of the head at a target reference posture from at least one deviated posture, of:
   measuring the real reference posture, to obtain several sets of data of real reference posture, and storing said sets of data,
   by means of a digital processing unit processing said sets of data of real reference posture to produce an optimal reference posture,
   wherein measuring the real reference posture comprises the location of singular points on at least one image of the subject,
   wherein the posture data comprises a pantoscopic angle value and cap angle value of the head of the subject, and
   wherein the pantoscopic angle value and cap angle value are determined by means of conditional probabilities depending on the previous sets of data of real reference posture and/or the previous type of deviated posture.

2. The process as claimed in claim 1, in which the real reference posture is measured during arrival of the head at the target reference posture.

3. The process as claimed in claim 1, in which at least two real reference postures are measured, said at least two real reference postures corresponding to two opposite deviated postures, and the optimal reference posture is obtained by taking an average of the reference postures measured during these two opposite deviated postures.

4. The process as claimed in claim 1, also comprising the determination of a confidence interval on said optimal reference posture.

5. The process as claimed in claim 1, in which the target reference posture corresponds to a posture in which the subject naturally looks at a determined target.

6. The process as claimed in claim 5, in which the target reference posture corresponds to the distant vision or near vision posture of the subject.

7. The process as claimed in claim 1, further comprising the application of weight to the data as a function of their respective relevance and of the type of associated deviation for evaluation of the optimal reference posture.

8. The process as claimed in claim 1, further comprising a step for determining the Frankfurt plane of the subject.

9. The process as claimed in claim 7, in which data of the Frankfurt plane are also integrated into the data taken into account for determination of the optimal reference posture and the confidence interval.

10. The process as claimed in claim 1, also comprising the progressive taking into account of an a priori model.

11. The process as claimed in claim 1, also comprising the extrapolation of supplementary data relative to reference postures which have not been taken by the subject from recorded data.

12. The process as claimed in claim 7, in which the singular points are supported by an accessory fixed on a glasses frame worn by the subject.

13. A process for estimation of a reference posture of a subject for the purposes of taking measurements for determination of parameters for the manufacture of a vision correction device, comprising the steps, for a plurality of arrivals of the head at a target reference posture from at least one deviated posture, of:
measuring the real reference posture, to obtain several sets of data of real reference posture, and storing said sets of data,
by means of a digital processing unit processing said sets of data of real reference posture to produce an optimal reference posture,
wherein measuring the real reference posture comprises the location of singular points on at least one image of the subject,
wherein the posture data comprises a pantoscopic angle value and cap angle value of the head of the subject, and
wherein the pantoscopic angle value and cap angle value are determined by means of conditional probabilities depending on the previous sets of data of real reference posture and/or the previous type of deviated posture,
further comprising the edition of posture data used for calculating the production parameters of the correction device, from
the confidence interval and the optimal reference posture of a set of data of a real reference posture or extrapolated from the sets of real data,
presentation of an image of the subject in this posture and/or the impact of the choice of this posture on the production parameters of the correction device.

14. A system for estimating a reference posture of a subject adapted to be implemented in a process 1 for estimation of a reference posture of a subject for the purposes of taking measurements for determination of parameters for the manufacture of a vision correction device, comprising the steps, for a plurality of arrivals of the head at a target reference posture from at least one deviated posture, of:
measuring the real reference posture, to obtain several sets of data of real reference posture, and storing said sets of data,
by means of a digital processing unit processing said sets of data of real reference posture to produce an optimal reference posture,
wherein measuring the real reference posture comprises the location of singular points on at least one image of the subject,
wherein the posture data comprises a pantoscopic angle value and cap angle value of the head of the subject, and
wherein the pantoscopic angle value and cap angle value are determined by means of conditional probabilities depending on the previous sets of data of real reference posture and/or the previous type of deviated posture, comprising:
means for measuring, during each arrival at the target reference posture, the real reference posture to obtain several sets of data of real reference posture,
means for storing said sets of data,
a digital processing unit adapted to process said sets of data of real reference posture to produce an optimal reference posture.

15. The system as claimed in claim 14, characterised in that the digital processing unit is also adapted to produce a confidence interval on said optimal reference posture.

16. The system as claimed in claim 14, characterised in that it also comprises a display device portable adapted to be worn by the subject, and in that the measuring means comprise an image-capture device fixed relative to the portable display device.

17. The system as claimed in claim 16, characterised in that the display device also comprises visual targets.

18. A computer program product comprising program code instructions for execution of the steps of the process as claimed in claim 1, when said program is executed by a computer.

* * * * *